United States Patent
Morizumi

[11] Patent Number: 5,702,349
[45] Date of Patent: Dec. 30, 1997

[54] ENDOSCOPE WITH ACUTELY ANGLED HANDLE AND ASSOCIATED FOCUS ADJUSTMENT MECHANISM

[75] Inventor: Masaaki Morizumi, Omiya, Japan

[73] Assignee: Fuji Photo Optical Co., Ltd., Saitama, Japan

[21] Appl. No.: 458,768

[22] Filed: Jun. 2, 1995

[30]  Foreign Application Priority Data

Jul. 7, 1994 [JP] Japan .................................. 6-156043

[51] Int. Cl.⁶ ................................................ A61B 1/00
[52] U.S. Cl. ................................... 600/131; 600/167
[58] Field of Search ............................ 600/131, 101, 600/102, 167; 433/29; D24/133, 137, 138; 606/205; 396/17, 103, 142, 470

[56]  References Cited

U.S. PATENT DOCUMENTS

| | | | |
|---|---|---|---|
| 3,677,262 | 7/1972 | Zukowski | 600/131 |
| 4,616,630 | 10/1986 | Arakawa | 600/131 |
| 4,915,626 | 4/1990 | Lemmey | 433/29 |
| 5,016,614 | 5/1991 | MacAllister | 600/131 |
| 5,088,819 | 2/1992 | Storz | 600/131 |
| 5,147,204 | 9/1992 | Patten et al. | 433/29 |
| 5,334,199 | 8/1994 | Yoon | 606/144 |
| 5,472,451 | 12/1995 | Freitas et al. | 606/205 |

*Primary Examiner*—Richard J. Apley
*Assistant Examiner*—John P. Leubecker
*Attorney, Agent, or Firm*—Oliff & Berridge, P.L.C.

[57]  ABSTRACT

A cylindrical grip member is connected to a back end of a body of an operation section at hand. The grip member is connected to face forward so that its axis can be at an acute angle against an axis of the back end of an insertion section. As for the grip member, it is possible to keep the body of the operation section horizontal if the grip member is held by a wrist in a natural way. Therefore, when this endoscope is used, the extra force does not have to be added to the wrist during observation. And, in the case that an angle formed by the body of the operation section and the grip member is set at 20°–45°, it is possible to hold the grip member in such a manner that an arm holding the grip member is put against the side of a human body, that is, the underarm is tightened, so the body of the operation section can be stably supported.

9 Claims, 6 Drawing Sheets

ENDOSCOPE WITH ACUTELY ANGLED HANDLE AND ASSOCIATED FOCUS ADJUSTMENT MECHANISM

BACKGROUND OF THE INVENTION

1. Field of the Invention

The present invention relates to an endoscope and more particularly to an endoscope which improves the operational efficiency of an observer.

2. Description of the Related Art

As for the conventional endoscope, as shown in FIG. 8 for example, a body of an operation section 1 is held by a left hand 2, an insertion section 3, which is connected to the body of the operation section 1, is inserted deep into an object of interest such as aircraft engine, etc., and the observed image sent from a forward end 4 of the insertion section 3 via an image transmission system provided at a flexible portion 5 and an elastic portion 6 is observed at an eyepiece section 7 provided at the back end of the body of the operation section 1.

And, in this endoscope, a focus adjustment ring 8 and an angle control ring 9 are provided at the body of the operation section 1, and when the focus adjustment ring 8 is rotated by an index finger, the focus of an objective lens system provided at the forward end 4 can be adjusted, and when the angle control ring 9 is rotated by a thumb, the flexible portion 5 can be curved in a desired direction.

It is preferable that the body of the operation section 1 is kept in such a manner that its longitudinal direction is substantially horizontal in a normal operation, in the light of a position of an object of interest and the like.

However, in the conventional endoscope, the body of the operation section 1 provided on the same axis as the longitudinal direction of the insertion section 3, is directly held by a hand, so the operator needs to bend his wrist toward himself. As a result, when the conventional endoscope is used, there is a problem in that the wrist gets tired during observation and the operational efficiency will be lowered.

SUMMARY OF THE INVENTION

The present invention has been developed in view of the above-mentioned circumstances, and has its aim the provision of an endoscope which can lighten the burden of an observer.

To achieve the above-mentioned object, the endoscope according to the present invention comprises a body of an operation section which is connected to an end of an insertion section, and a grip member which is connected with a back end of the body of the operation section in such a manner that an axis of the end of the Grip member is at an acute angle against an axis of the end of the insertion section.

According to the present invention, since the grip section is provided to face forward so as to be at an acute angle against the axis of the body of the operation section at hand at the end of the body of the operation section at hand, the body of the operation section at hand is substantially horizontal when the grip is held by the wrist in a normal way.

BRIEF DESCRIPTION OF THE DRAWINGS

The exact nature of this invention, as well as other objects and advantages thereof, will be readily apparent from consideration of the following specification relating to the accompanying drawings, in which like reference characters designate the same or similar parts throughout the figures and wherein.

DESCRIPTION OF THE PREFERRED EMBODIMENT

Detailed description will hereunder be given of the preferred embodiment of an endoscope according to the present invention with reference to the accompanying drawings.

Figure 1:
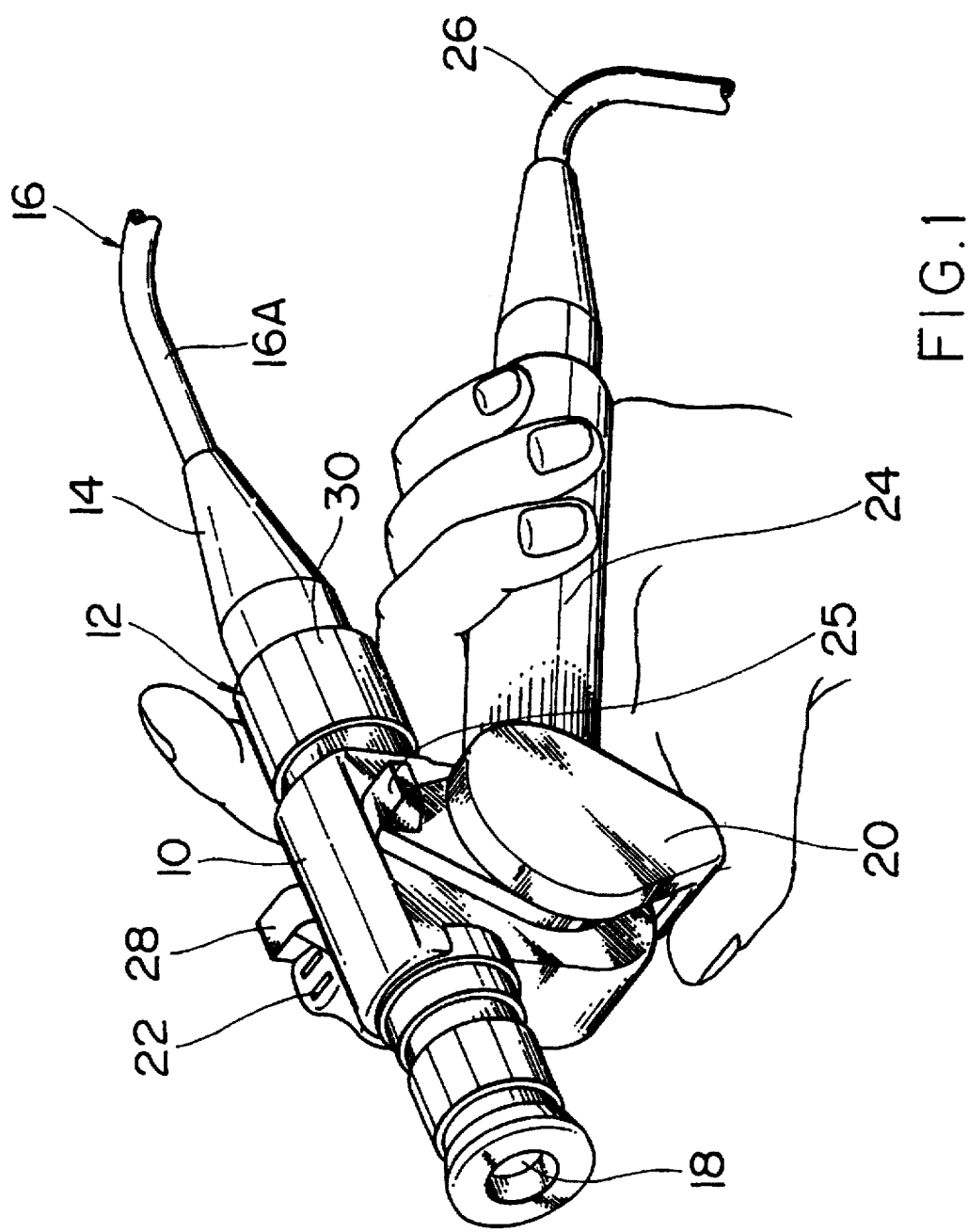
FIG. 1 is a perspective view illustrating an embodiment of an endoscope according to the present invention.

FIG. 1 is a perspective view illustrating an embodiment of the endoscope according to the present invention.

As shown in FIG. 1, a connecting portion 14 is attached at the forward portion of a body of an operation section 10 of the endoscope via a focus adjustment device 12, which will be described later, and the insertion section 16 of the endoscope is connected with the forward end of the connecting portion 14. The connecting portion 14 is connected to an end 16A of the insertion section on the substantially same axis. The insertion section 16 has a predetermined length so as to be inserted into an observation section, and the observed image sent from the forward end, which is not shown in the drawing, is observed through the eyepiece section 18 provided at the back end of the body of the operation section 10. Furthermore, angle levers 20 and 22 for controlling the angle and brake knobs 25 and 28 for adjusting the frictional torque acting on the respective levers 20 and 22 are provided at the both sides of the body of the operation section 10. The angle levers 20 and 22 for controlling the angle are rotated so that the flexible portion of the insertion section 16, which is not shown in the drawing, can be curved vertically and horizontally in the desired direction as well known.

As shown in FIG. 1, the focus adjustment device 12 is provided with a focus adjustment ring 30 which can be operated from outside, and the focus adjustment ring 30 is rotatably arranged on the same axis as the axis B (Refer to FIG. 2) of the end 16A of the insertion section 16, so that it can be operated with an index finger of the hand holding the grip member 24.

Figure 3:
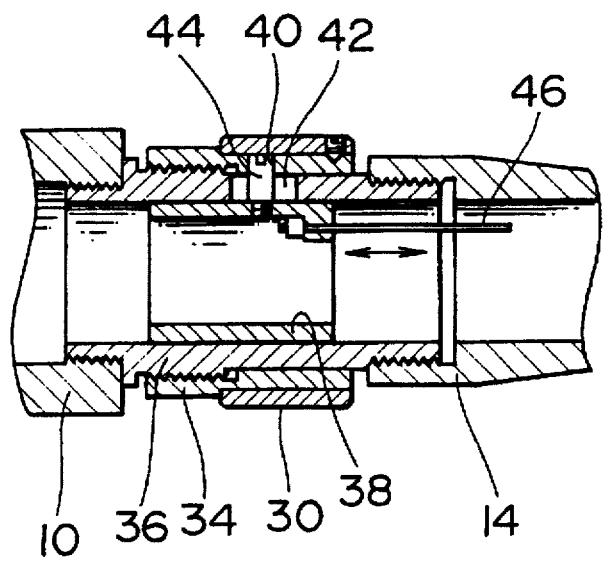
FIG. 3 is a sectional view illustrating an embodiment of a focus adjustment system applied to the endoscope of the present invention.
Figure 4:
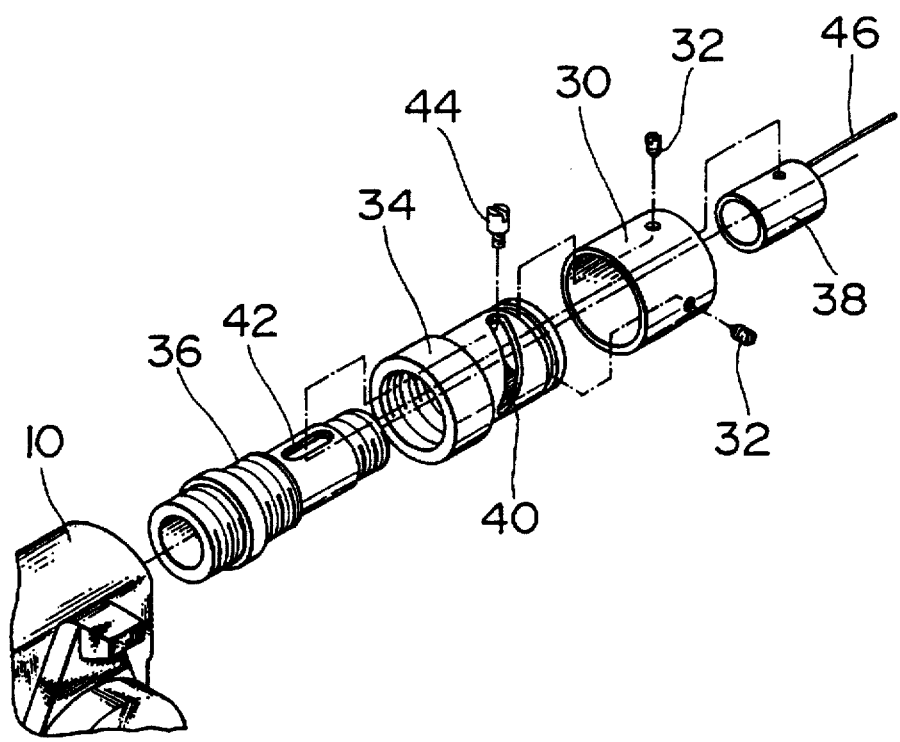
FIG. 4 is a perspective view illustrating the structure of the focus adjustment system.

As shown in FIGS. 3 and 4, the focus adjustment ring 30 is fixed at a focus cam ring 34 by screws 32 and 32. The focus cam ring 34 is screwed with a base ring 36 which connects the body of the operation section 10 and the connecting portion 14, and a focus actuating cylinder 38 is inserted and arranged in the base ring 36. A cam pin 44 is fixed at the focus actuating cylinder 38 via a cam groove 40 formed at the focus cam ring 34 and a slot-shaped guide groove 42 formed at the base ring 36. And, the end of the focus adjustment wire 46 is fixed at the focus actuating cylinder 38, and the forward end of the focus adjustment wire 46 is fixed at the focus lens camera cone arranged at the forward end of the insertion section 16. The focus lens camera cone is arranged along an optical axis so it can be movable both forward and backward, and is forced by the forcing means in the direction opposite to the body of the operation section 10.

Therefore, according to the focus adjustment device 12 of this embodiment, the focus cam ring 34 rotates when the focus adjustment ring 30 is rotated, and the cam pin 44 moves straight along the guide groove 42 due to the function of the cam groove 40 and the guide groove 42. As a result, the focus actuating cylinder 38 connected with the cam pin 44 slides against the base ring 36, the focus adjustment wire 46 is pushed and pulled, and the focus lens camera cone moves both forward and backward, so that the focus adjustment can be carried out.

On the other hand, as shown in FIG. 1, the grip member 24 is connected to the lower portion of the body of the operation section 10, and the grip member 24 has a cylindrical shape convenient for an observer to hold. And, as shown in FIG. 2, the grip member 24 is inclined in such a manner that its axis A is at an acute angle θ against the axis B of the end 16A of the insertion section 16.

And, a light guide cable 26 is inserted into the grip member 24. The forward end of the light guide cable 26 is inserted and arranged at the forward end of the insertion section 16 via the body of the operation section 10, the connecting portion 14, and the insertion section 16 from the grip member 24, and illuminates the observation section from the forward end.

According to the endoscope constructed in the above-mentioned manner, it is possible to horizontally hold the body of the operation section 10 when the grip member 24 is held by the wrist in a normal way. Therefore, if the endoscope of this embodiment is used, it is unnecessary to add the extra force to the wrist during observation.

Figure 2:
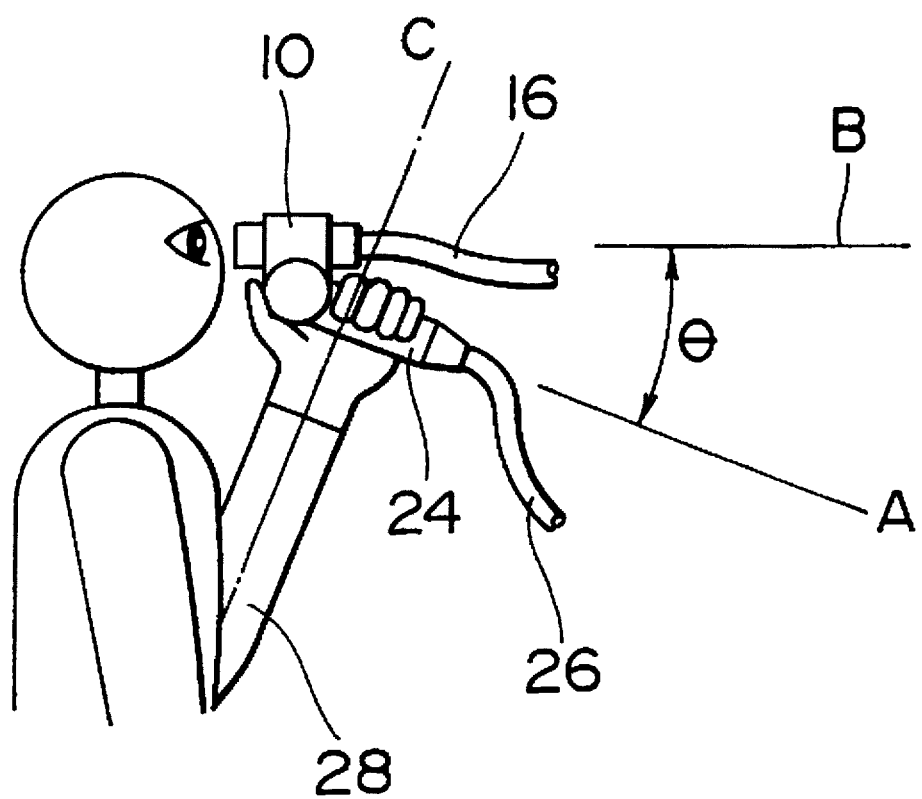
FIG. 2 is an explanatory view illustrating the case when an endoscope of the present invention is used.

And, in the case that the acute angle θ is set at 20°–45°, as shown in FIG. 2, it is possible to hold the grip member 24 in a state that the arm holding the grip member 24 is put against the human body, that is, with an underarm tightened, so that the body of the operation section 10 can be stably supported.

Furthermore, if the angle formed by an axis C of the arm 28 and the axis A of the grip member 24 is set at 90°, no extra force is applied to the wrist holding the grip member 24.

And, in the endoscope of this embodiment, when the grip member 24 is held by the left hand as shown in FIG. 1, the focus adjustment ring 30 is provided at a position to be operated by the index finger, so that the focus adjustment can be carried out.

In this embodiment, the explanation was given of the industrial endoscope, but the present invention is not limited to this and can be applied to a medical endoscope.

As explained above, according to the endoscope of the present invention, because the grip member is provided to face forward so as to be at an acute angle against the axis of the body of the operation section and the body of the operation section is substantially horizontal when the grip member is held by the wrist in a natural way, the operator can stably handle the endoscope and does not get tired even if he uses the endoscope for a long time.

Figure 5:
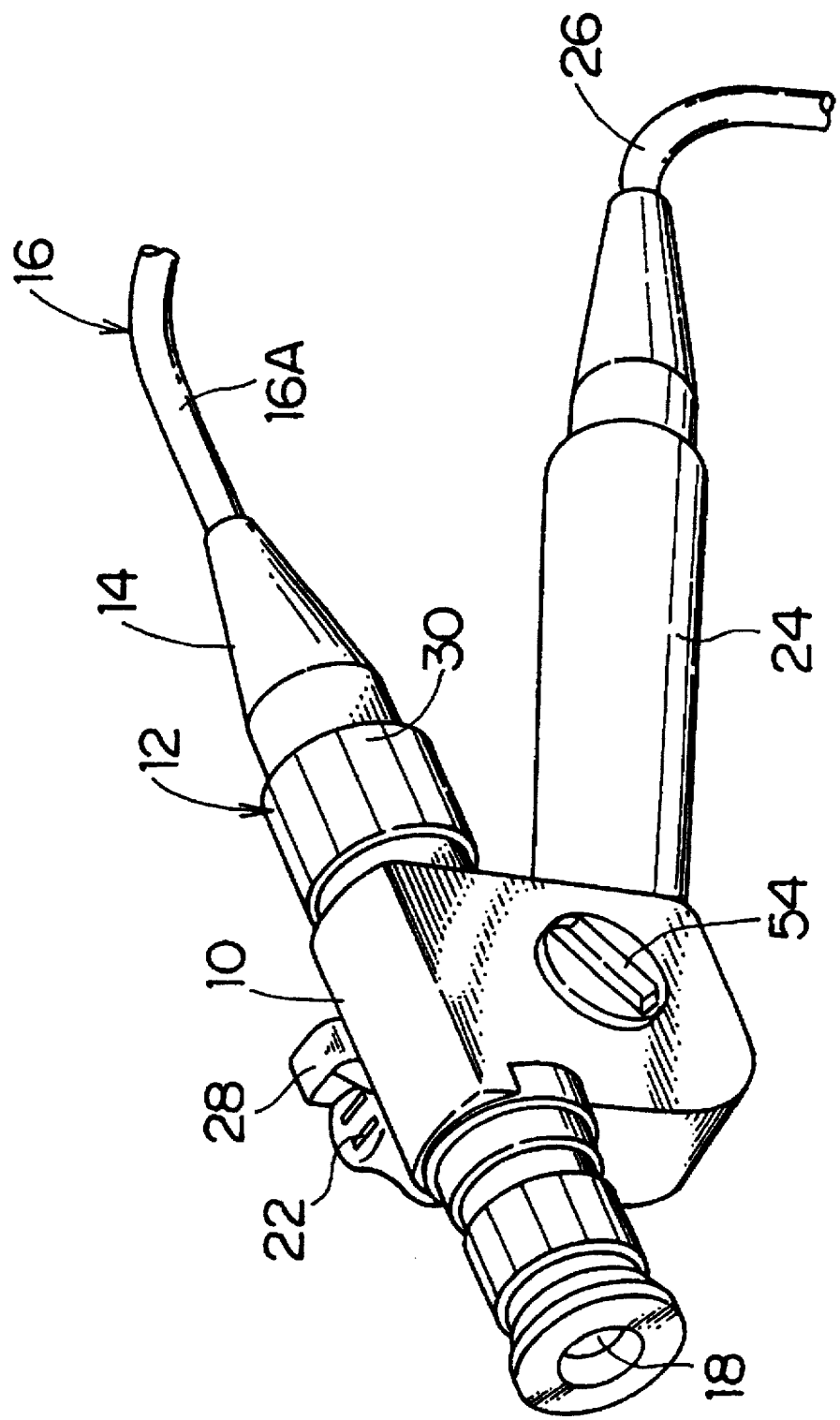
FIG. 5 is a perspective view illustrating a second embodiment of the endoscope according to the present invention.

FIG. 5 is a perspective view illustrating the external appearance of the endoscope according to the second embodiment of the present invention, and the same marks are put on the same or similar members as those of the first embodiment shown in FIGS. 1–4.

Figure 6:
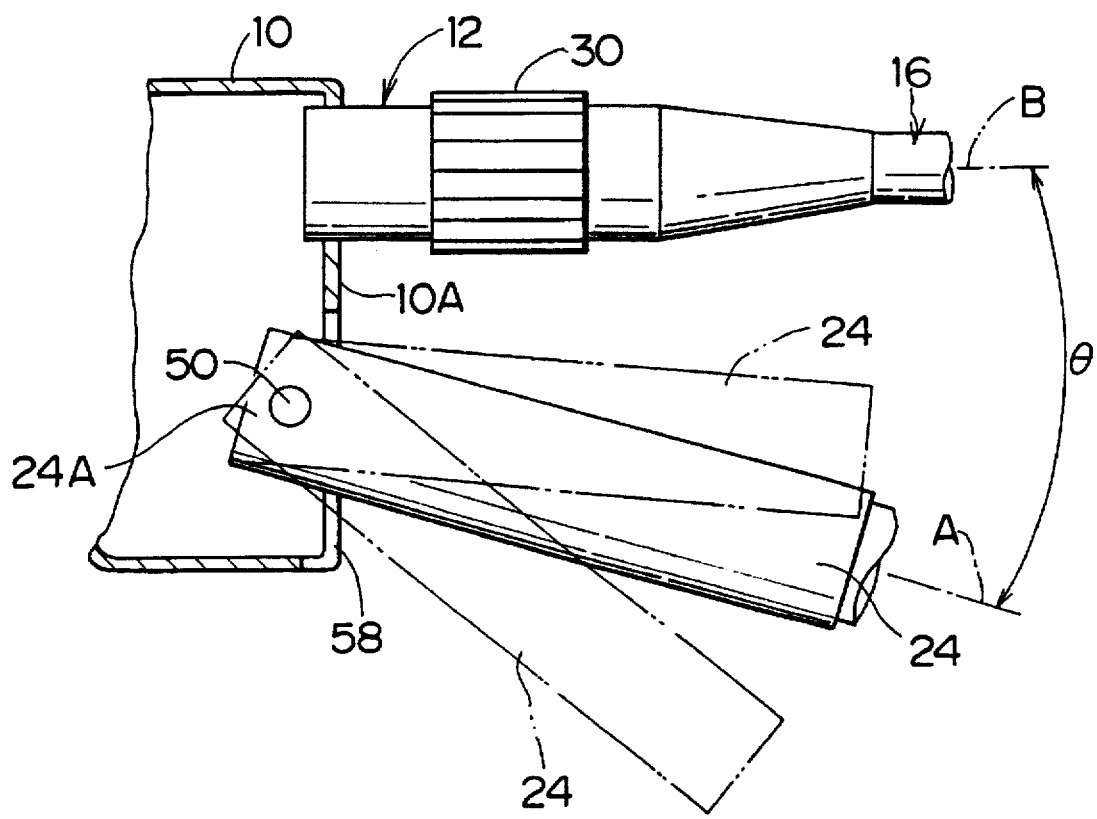
FIG. 6 is a side view including a partially sectional view illustrating the state that a grip member rotates.
Figure 7:
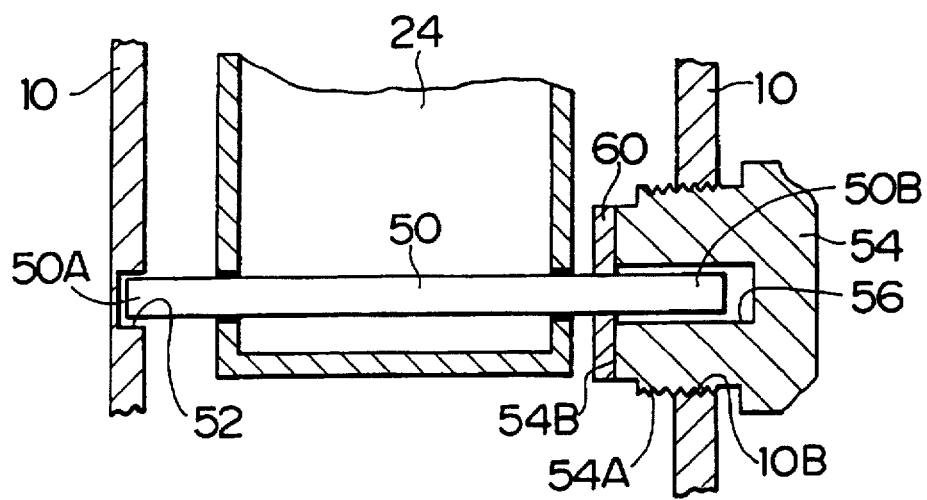
FIG. 7 is a sectional view illustrating the rotational lock mechanism of the grip member; and, FIG. 8 is a perspective view illustrating an embodiment of the conventional endoscope.
Figure 8:
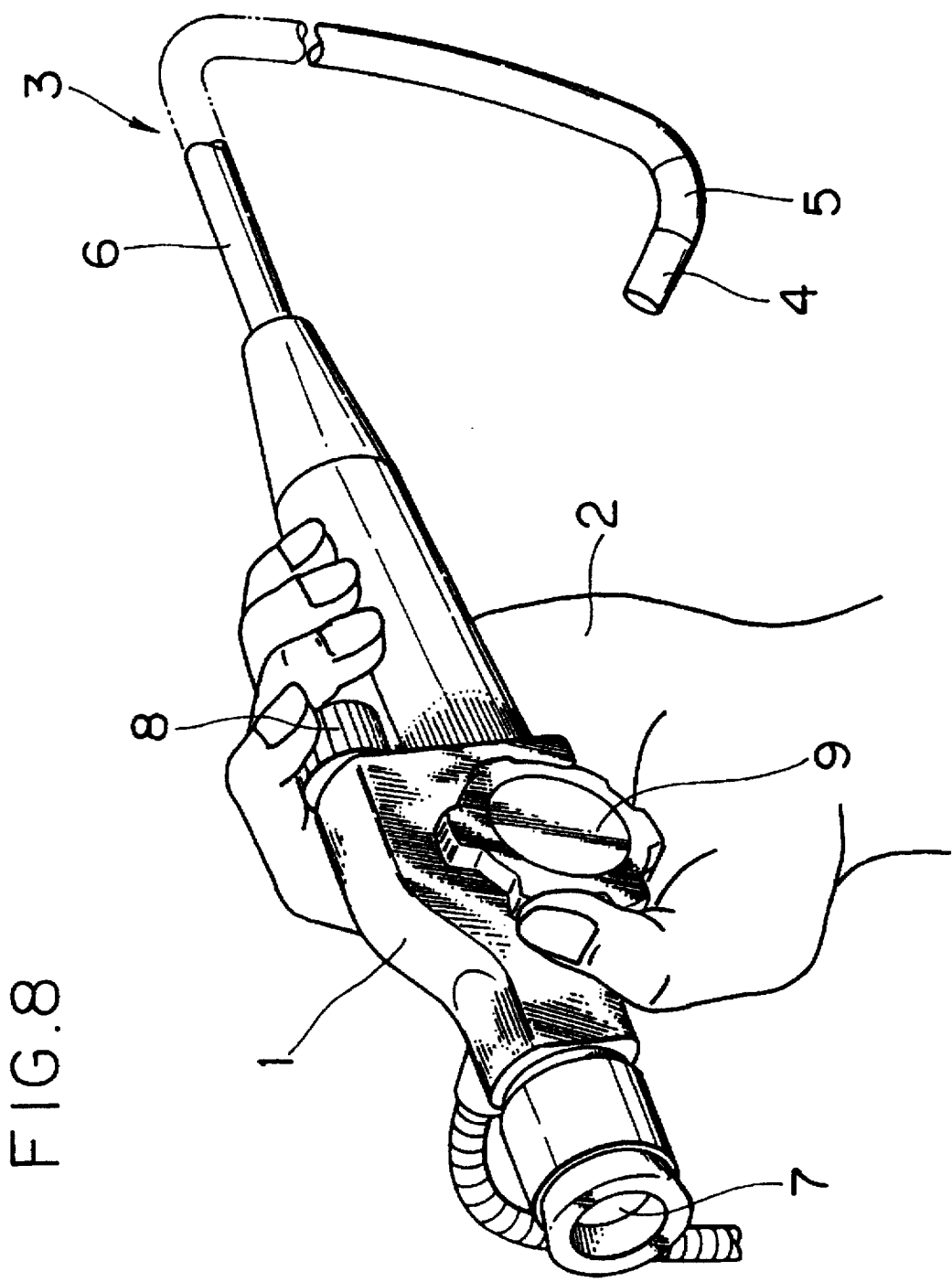

In the endoscope shown in FIG. 5, the grip member 24 is rotatably supported at the body of the operation section 10, and the angle formed by the axis A of the grip member 24 and the axis B of the end 16A of the insertion section 16 is adjustable. As for the structure, an axis 50 is fixed at an end 24A of the grip member 24 as shown in FIG. 6. As shown in FIG. 7, left end 50A is rotatably supported at a depression 52 formed at the side of the body of the operation section 10, and a right end 50B is rotatably supported at a hole part 56 formed at a lock knob 54. And, an aperture 58, which allows the grip member to rotate, is opened at a front surface 10A of the body of the operation section 10 as shown in FIG. 6.

Incidentally, as shown in FIG. 7, in the lock knob 54, a male screw part 54A is screwed with a female screw part 10B formed at the body of the operation section 10. And, a frictional plate 60 is arranged at a position to face the left end surface 54B of the lock knob 54. The frictional plate 60 is fixed at the axis 50. Therefore, when the lock knob 54 is screwed into the body of the operation section 10, as shown in FIG. 7, the left end surface 54B pushes and contacts the frictional plate 60, a frictional force generated between the left end surface 54B and the frictional plate 60 is transmitted to the axis 50, and when the frictional force exceeds the predetermined value, the rotation of the axis 50 is locked. As a result, the rotation of the grip member 24 can be locked, and the angle formed by the axis A of the grip member and the axis B of the end 16 A of the insertion section 16 can be fixed at a desired angle.

Therefore, according to the endoscope of the second embodiment, the grip member can be freely set at an angle convenient for holding.

It should be understood, however, that there is no intention to limit the invention to the specific forms disclosed, but on the contrary, the invention is to cover all modifications, alternate constructions and equivalents falling within the spirit and scope of the invention as expressed in the appended claims.

What is claimed is:

1. An endoscope, comprising:
    a body section;
    a rotatable operating section having a longitudinal axis, a first end mounted to the body section and a second end;
    an insertion element comprising an insertion cable, a wire extending through the insertion cable and a lens system connected to the wire and mounted in a distal end of the insertion cable, the insertion element mounted at a proximal end to the rotatable operating section and extending from the second end thereof;
    a grip section having a longitudinal axis and mounted to the body section and extending toward the insertion element such that the longitudinal axis of the rotatable operating section and the longitudinal axis of the grip section intersect at an acute angle; and
    focus adjustment means in the rotatable operating section for translating a rotation of the rotatable operating section into a longitudinal movement of the wire, wherein the rotatable operating section is disposed adjacent to an intersection between the body section and the grip member.

2. The endoscope according to claim 1, wherein the acute angle is in a range of 20°–45°.

3. The endoscope according to claim 1, wherein the grip member is rotatably mounted to the body section thereby making the acute angle adjustable.

4. The endoscope according to claim 3, further comprising a lock member for locking a position of the grip member relative to the body.

5. The endoscope according to claim 4, wherein the acute angle is adjustable over a range from 20° to 45°.

6. A hand holdable endoscope, comprising:

an operation section having a longitudinal axis, a first end and a second end;

a rotatable focus adjustment section having a longitudinal axis, a first end and a second end, the first end mounted to the first end of said operation section, the longitudinal axes of said focus adjustment section and said operation section being aligned with one another;

a connection portion having a first end and a second end, the first end connected to the second end of said focus adjustment section;

an insertion section connected to and extending from the second end of said connection portion and having a forward end containing a focus lens system;

a grip member mounted to said operation section and having a longitudinal axis, said grip member extending from said operation section toward said insertion section in such a manner that the longitudinal axis of said grip member is at an acute angle against the longitudinal axes of said focus adjustment section and said operation section; and a focus adjustment wire extending through said insertion section, said focus adjustment wire fixed at one end to said focus adjustment section and at an opposite end to said focus lens system, whereby the focus adjustment section is adapted to be rotated by a finger of a hand of an operator holding the grip member.

7. The endoscope according to claim 6, wherein the acute angle formed by the extension of the longitudinal axes and the extended axis of grip member is set within a range from 20° to 45°.

8. The endoscope according to claim 6, wherein the mounting of said grip member is a rotatable mounting to the operation section, so that the acute angle formed by the extension of the longitudinal axes and the extended axis of the grip member is adjustable.

9. The endoscope according to claim 8, further comprising a lock member to retain the angle at a desired angle.

* * * * *